United States Patent
Gupta et al.

(10) Patent No.: US 7,114,374 B2
(45) Date of Patent: Oct. 3, 2006

(54) SENSITIVE SPINLINE-TYPE EXTENSIONAL VISCOMETER FOR MOBILE LIQUIDS EMPLOYING VERY SMALL LIQUID VOLUMES

(75) Inventors: Rakesh K. Gupta, Morgantown, WV (US); Sushant Agarwal, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 185 days.

(21) Appl. No.: 10/482,232

(22) PCT Filed: Jun. 21, 2002

(86) PCT No.: PCT/US02/19745

§ 371 (c)(1),
(2), (4) Date: Jun. 10, 2004

(87) PCT Pub. No.: WO03/001157

PCT Pub. Date: Jan. 3, 2003

(65) Prior Publication Data

US 2004/0206163 A1    Oct. 21, 2004

Related U.S. Application Data (60) Provisional application No. 60/300,030, filed on Jun. 21, 2001.

(51) Int. Cl.
*G01N 11/06* (2006.01)

(52) U.S. Cl. .................................... 73/54.07

(58) Field of Classification Search ............ 73/54.06, 73/54.04, 54.05, 54.07, 54.08, 54.11, 54.43

See application file for complete search history.

(56) References Cited

U.S. PATENT DOCUMENTS

| | | | | |
|---|---|---|---|---|
| 3,277,694 | A | | 10/1966 | Cannon et al. ................. 73/55 |
| 3,520,179 | A | * | 7/1970 | Reed ............................ 73/54.04 |
| 3,864,962 | A | | 2/1975 | Stark et al. .................... 73/55 |
| 3,911,728 | A | * | 10/1975 | Fixot .......................... 73/54.04 |
| 4,425,790 | A | * | 1/1984 | Bice et al. ................... 73/54.05 |
| 4,441,358 | A | | 4/1984 | Osborne ........................ 73/55 |
| 5,357,784 | A | | 10/1994 | Collier ....................... 73/54.14 |
| 5,365,776 | A | | 11/1994 | Lehmann et al. ........... 73/54.07 |
| 5,456,105 | A | | 10/1995 | James ........................ 73/54.01 |
| 5,756,883 | A | | 5/1998 | Forbes ....................... 73/54.05 |

(Continued)

OTHER PUBLICATIONS

R.C. Chan and R.K. Gupta, "Fiber Spinning of Very Dilute Solutions of Polyacrylamide in Water," *Journal of Non-Newtonian Fluid Mechanics*, 30(1988) 267-283.

*Primary Examiner*—Michael Cygan
(74) *Attorney, Agent, or Firm*—Steptoe & Johnson PLLC (57) ABSTRACT

A method for making fluid elasticity measurements using an extensional viscometer (100) is disclosed, where stress is not directly measured but is inferred from an accurate measurement of the change in the rate of flow of a liquid during passage through a vertical capillary (104). The flow rate changes when the liquid jet, also called the liquid filament, leaving a first capillary (104), is stretched by the application of vacuum forces. Steady flow is established almost instantly by using a constant liquid head (102, 118) above the capillary, and the flow rate is determined by timing the interval for liquid to drain between two marks (110, 112) on the liquid reservoir surface. Extensional viscosity can be calculated as a ratio of the tensile stress and stretch rate of the liquid at different axial positions.

20 Claims, 2 Drawing Sheets

U.S. PATENT DOCUMENTS 6,386,016 B1  5/2002  Gleissle .................... 73/54.01

6,393,898 B1  5/2002  Hajduk et al. ............. 73/54.05

\* cited by examiner

SENSITIVE SPINLINE-TYPE EXTENSIONAL VISCOMETER FOR MOBILE LIQUIDS EMPLOYING VERY SMALL LIQUID VOLUMES

CROSS REFERENCE TO RELATED APPLICATIONS

This application claims the benefit of U.S. Application Ser. No. 60/300,030, filed Jun. 21, 2001.

BACKGROUND OF THE INVENTION

1. Field of Invention

This invention relates to rheometry, and, more specifically, to a method and apparatus for measuring fluid stresses in extension.

2. Related Art

Mobile polymer solutions, liquid-liquid emulsions, and dilute solid-in-liquid suspensions show flow behavior in which the observed stress has an origin that is partly viscous and partly elastic. These viscous and elastic properties can be measured using a variety of viscometers. Knowledge of these properties is needed for purposes of material characterization, product differentiation, product formulation, and quality control.

Many fluids of industrial interest show only low levels of elasticity, and researchers have found that the use of an extensional flow field is best suited for fluid elasticity measurement. However, extensional viscometers that can make measurement under flow conditions representative of industrial operations require large liquid volumes on the order of one quart. This is because flow has to be set up and a steady state established before the fluid stress can be measured. This is often problematic because sample quantities are often limited due to the expense of the liquid to be measured.

When limited samples are available, fluid recirculation is necessary. Fluid recirculation is undesirable because polymer chain scission happens easily during stretching. Furthermore, in applications such as aerosol formation during agricultural pesticide and herbicide spraying, and also in inkjet printing, the liquids of interest are relatively inelastic and have shear viscosities that are as low as 5 or 6 mPa·s. Measuring extensional viscosity of these liquids is extremely difficult. Therefore, there is a need for a method and apparatus capable of making fluid elasticity measurements with only small volumes of fluid and without the need for re-circulating the sample. There is a further need for a method and apparatus that can make these measurements for relatively inelastic fluids having low shear viscosities.

SUMMARY OF THE INVENTION

This invention solves the problems encountered when using conventional viscometers to measure extensional viscosity of fairly inelastic liquids. As such, a news method and apparatus is available for measuring fluid stresses using very small liquid volumes, thereby eliminating the need to re-circulate the liquid being measured.

One aspect of the invention is a method for determining tensile stress within a liquid, including the steps of: measuring the liquid's gravity-driven drainage time; measuring the liquid's stretched drainage time; and calculating the tensile stress of the liquid as a function of the difference between the liquid's gravity-driven drainage time and the liquid's stretched drainage time.

Another aspect of the invention is a method for determining extensional viscosity of a solution, including the steps of: calculating tensile stress within the solution; calculating the solution's stretch rate; and calculating extensional viscosity of the solution as a ratio of tensile stress to stretch rate.

Another aspect of the invention is an extensional viscometer for measuring tensile stress within a liquid, including a liquid reservoir; a first capillary through which liquid drains, connected to the liquid reservoir; and a second capillary positioned beneath the first capillary thereby creating a gap between the first and second capillaries, such that liquid is stretched as it passes from the first capillary to the second capillary.

Another aspect of the invention is a method for determining extensional viscosity of a liquid, including the step of inferring fluid stress by measuring change in flow rate of the liquid during passage through a vertical capillary.

A feature of the invention is the calculation of tensile stress of a liquid as a function of the difference between the liquid's free flow, or gravity-driven flow rate, and its stretched flow rate.

Another feature of the invention is the calculation of extensional viscosity of a liquid as a ratio of the liquid's tensile stress and stretch rate.

An advantage of the invention is that it uses small liquid volumes to make fluid elasticity measurements.

Another advantage of the invention is that it obviates the need for re-circulating the liquid sample for which elasticity is being measured.

Another advantage of the invention is that it makes fluid elasticity measurements that are more sensitive than existing extensional viscometers.

Another advantage of the invention is that it allows for the measurement of extensional viscosity in liquids that are relatively inelastic and that have low shear viscosities.

EMBODIMENTS OF THE INVENTION

The present invention provides a method and apparatus for measuring small fluid stresses in extension. Fluid stress in extension is used to measure extensional viscosity.

When considering gravity-driven flow of a liquid from a reservoir through a capillary of radius (R) and length (l), the time of drainage can be measured as the liquid falls from one level to another. If the liquid filament exiting from the capillary is stretched, the flow rate changes significantly due to the presence of tensile stress, which changes the time of drainage for the liquid level to fall. In the present invention, the two drainage times, gravity-driven drainage time ($t_1$) and stretched drainage time ($t_2$), are measured and used to calculate the tensile stress ($\sigma_{ext}$). From the liquid's filament profile, the stretch rate can be calculated, and this, together with the measured tensile stress, gives the extensional viscosity.

Figure 1:
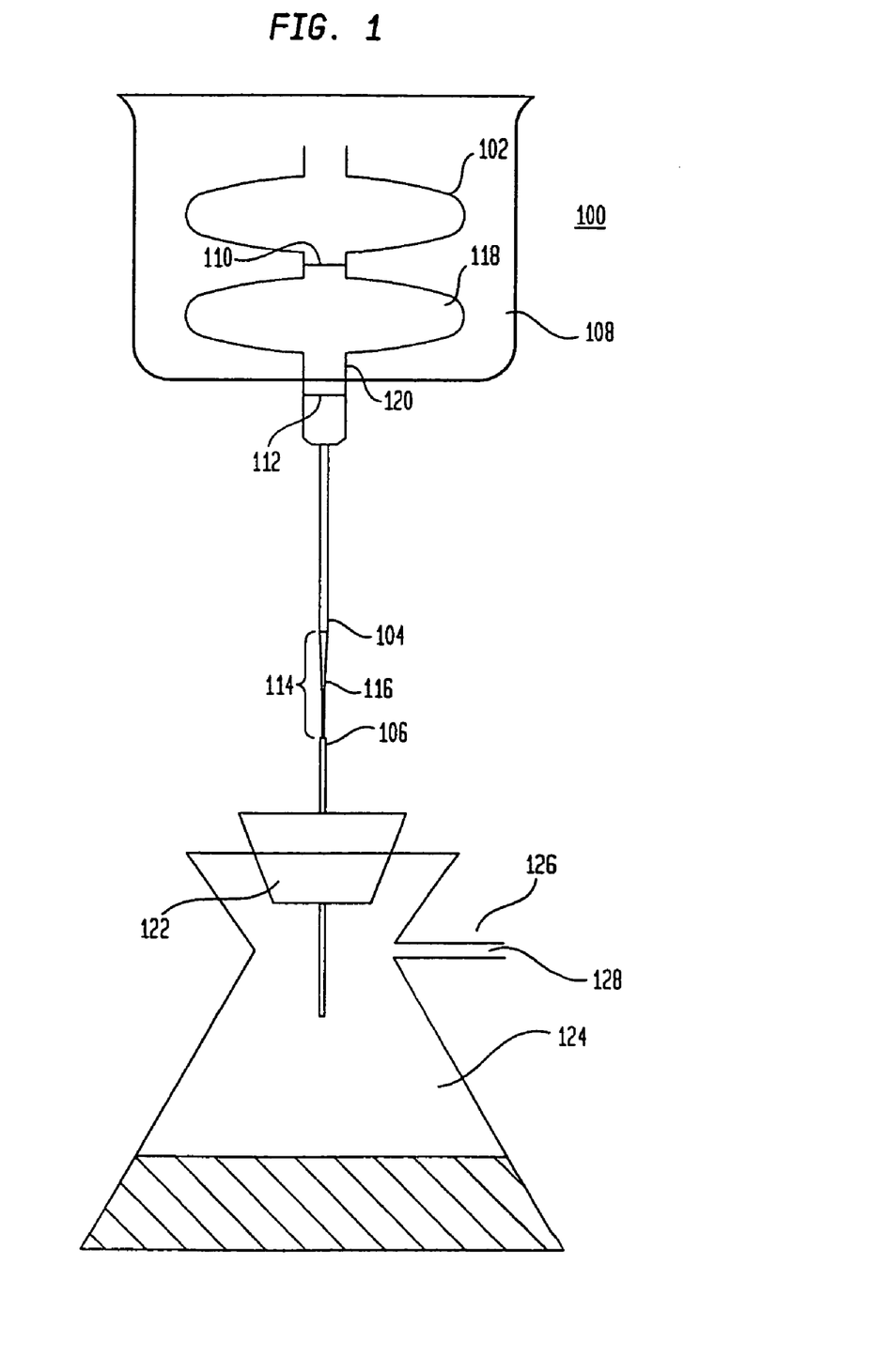
FIG. 1 shows an embodiment of an extensional viscometer.

For a Newtonian liquid of shear viscosity $\eta$, the tensile stress at the exit of the capillary can be calculated as follows:

$$\sigma_{ext} = \frac{8\eta lV}{\pi R^4}\left[\frac{1}{t_2} - \frac{1}{t_1}\right]$$

where V is the volume of liquid contained between a first mark 110 and a second mark 112 as shown in FIG. 1. Note that this equation follows from the well-known Hagen-Poiseuille equation. However, corrections must be made for non-Newtonian character when polymer solutions are used. For example, in the case of a solution that follows power law behavior, the following equations must be used to calculate the tensile stress:

$$\frac{V}{t_1} = \frac{\pi n}{3n+1}\left(\frac{\rho gl + P_0}{2Kl}\right)^{\frac{1}{n}}\left(\frac{d}{2}\right)^{\frac{3n+1}{n}}$$

$$\frac{V}{t_2} = \frac{\pi n}{3n+1}\left(\frac{\rho gl + P_0 + \sigma_{ext}}{2Kl}\right)^{\frac{1}{n}}\left(\frac{d}{2}\right)^{\frac{3n+1}{n}}$$

in which K and n are the fluid consistency index and power-law index respectively. Also, $\rho$ is the liquid density, g is the acceleration due to gravity and $p_0$ is the gage pressure at the capillary entrance.

FIG. 1 shows an embodiment of a viscometer 100 for measuring extensional viscosity of a liquid. The viscometer 100 includes a liquid reservoir 102, a first capillary 104 connected to the liquid reservoir 102, and a second capillary 106. The viscometer 100 optionally, but preferably, includes a water bath 108 in which the liquid reservoir 102 may be immersed. The temperature of the water bath 108 may be maintained by a circulator, such as a Fisher Scientific Isotemp circulator, or other means known to one of ordinary skill in the art. The circulator is not shown in the drawings for convenience purposes only.

The liquid reservoir 102 preferably is made of glass, but optionally may be made of plastic, stainless steel, or other materials known to one of ordinary skill in the art. The liquid reservoir 102 holds the liquid for which fluid stresses are to be determined. The liquid reservoir 102 optionally, but preferably, is tapered with at least one collection area 118 positioned above a neck 120 through which the liquid flows. The liquid reservoir 102 preferably has two marks; a first mark 110 indicating the level to which the reservoir is to be filled and a second mark 112 indicating the level to which the reservoir is to be drained. The marks are useful for measuring drainage time of the liquid.

The liquid reservoir 102 optionally, but preferably, is immersed in the water bath 108. The temperature of the water in the water bath 108 preferably is maintained at a constant temperature between about 23° C. to about 27° C., with a most preferred temperature of about 25° C. The water bath 108 thus maintains the liquid in the liquid reservoir 102 at a constant temperature.

The first capillary 104 is communicably connected, by means known to those of ordinary skill in the art, to the liquid reservoir 102 for draining liquid from the liquid reservoir 102. The first capillary 104 preferably is made of thin wall stainless steel, but optionally may be made of glass or plastic. It is desirable that the diameter of the first capillary 104 be large enough that liquid being drained from the liquid reservoir 102 does not drip from the first capillary 104. However, it is also desirable that the diameter of the first capillary 104 be small enough that liquid being drained from the liquid reservoir 102 does not drain too rapidly. Thus, the first capillary 104 should have a diameter such that a slow, steady stream is obtained as liquid drains from the liquid reservoir 102 and through the first capillary 104. The diameter of the first capillary 104 preferably is between about 0.10 cm and about 0.19 cm, with the most preferred diameter being between about 0.127 cm and 0.16 cm. The first capillary 104 optionally has a length of between about 2 cm and about 10 cm, with a preferred length of about 3 cm to about 8 cm, and a most preferred length of about 5 cm. While the most preferred length and width of the first capillary 104 may vary depending on the liquid being tested, one of ordinary skill in the art will be able to determine a preferred length and diameter of the first capillary 104 without undue experimentation.

A second capillary 106 is positioned beneath the first capillary 104 such that a gap 114 exists between the first and second capillaries 104, 106. The second capillary 106 is positioned by means known to those of ordinary skill in the art, such as, by inserting the second capillary 106 through a hole in a stopper 122 and inserting the stopper 122 in a flask 124. The flask 124 optionally, but preferably, includes an extension 126 for connecting the flask 124 to a means for generating negative pressure within the flask 126. This negative pressure, e.g., vacuum pressure, draws air from the flask 124 via an opening 128 in the extension 126. This pressure helps stretch the liquid as it flows from the first capillary 104 into the second capillary 106.

The size of the gap 114 may be varied depending on the liquid being drained from the liquid reservoir 102, the stretch rate of the liquid, and the amount of pressure exerted through the flask 124. The liquid exiting the first capillary 104 is stretched as it traverses the gap 114 between the first capillary 104 and the second capillary 106, thereby establishing a liquid filament profile 116. One of ordinary skill in the art will be able to determine a preferred gap 114 distance between the first capillary 104 and the second capillary 106 without undue experimentation. The second capillary 106 preferably is made of thin wall stainless steel, but optionally may be made of glass or plastic. The diameter of the second capillary 106 preferably is equal to or less than the diameter of the first capillary 104.

After selecting the appropriate length and diameters for the first and second capillaries 104,106, gravity-driven drainage rate (also called free flow drainage rate) of the liquid is measured by filling the liquid reservoir 102 to the first mark 110 with the liquid, and allowing the liquid to obtain a predetermined constant temperature. The time of drainage is then measured for free flow through the first capillary 104 as the liquid level drops from the first mark 110 to the second mark 112. Free flow, also called gravity-driven flow, means flow that results simply from the pressure of gravity exerted on the column of liquid. Free flow is not facilitated by additional external pressures, i.e., vacuum pressure.

Stretched drainage rate is measured by again filling the liquid reservoir 102 to the first mark 110 with the liquid. The liquid is again drained through the first capillary 104, however, as the liquid emerges from the first capillary 104 it is stretched as it exits the first capillary 104 and enters the second capillary 106. Stretching of the liquid as it leaves the first capillary 104 and enters the second capillary 106 is accomplished by applying vacuum through the second capillary 106 to suction the liquid into the second capillary 106. The connection of the flask 124 to the source of vacuum pressure is well known in the art, and thus is not included in the drawings for convenience purposes. The stretch rate can be adjusted by altering the gap 114 between the first and second capillaries 104,106. In one embodiment, the gap 114 is altered by sliding the second capillary 106, either up or down as desired, in a hole in the stopper 122. The stretched drainage time is measured as the liquid level drops from the first mark 110 to the second mark 112 in the liquid reservoir 102. The difference between the free flow drainage rate and the stretched drainage rate preferably is greater than or equal to one second thereby assuring the accuracy of the measurements.

Figure 2A:
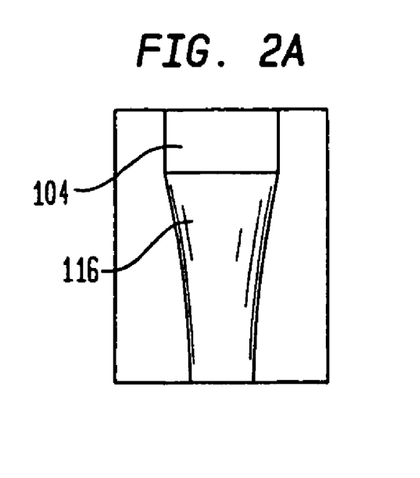
FIG. 2A shows a stretched liquid filament profile.
Figure 2B:
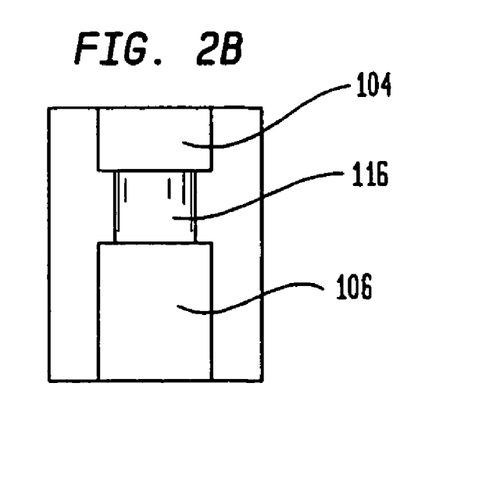
FIG. 2B shows an unstretched liquid filament profile.

Fluid stresses, then, can be inferred as a result of data obtained while determining the liquid's change in flow rate through a vertical capillary as a result of stretching. For example, the liquid's filament profile during stretching can be calculated by capturing an image of the liquid, i.e., the liquid filament 116 (also called the liquid jet), as it emerges from the first capillary 104 during stretching through the gap 114. The image may be obtained by using a digital camera fitted with a zoom lens. For illustration purposes, compressed images of the stretched filament and the free flowing liquid filament are shown in FIGS. 2A and 2B respectively. Using the image of the stretched filament profile, diameter as a function of distance along the axis can be measured for the liquid filament. By knowing the volumetric flow rate, the stretch rate can be calculated along the axis. A typical stretch rate variation with the filament length in case of a polymer solution is shown in Table 1, which shows that very high stretch rates are obtainable as one moves down along the filament axis.

TABLE 1

Stretch rate as a function of distance from capillary exit for set 1 in Table 6.

The tensile stress at the exit of the upper capillary can be calculated using the rate of change in the liquid's flow rate during stretching. To calculate the tensile stress at any position along the axis of the stretching filament, the method employed by R. C. Chan, R. K. Gupta, and J. T. Sridhar, NON-NEWTONIAN FLUID MECHANICS 30, pp. 267–283 (1988) is used. This utilizes a momentum balance along the axis of the filament. Thus, by knowing the tensile stress and the stretch rate at different axial positions, the extensional viscosity can then be calculated as a ratio of these two quantities.

EXAMPLES

Calibration

For Newtonian liquids the ratio of extensional viscosity, also known as Trouton's ratio, is three. Therefore, to calibrate the equipment a Newtonian calibration standard mineral oil obtained from Cannon Instrument Company, State College, Pa., of shear viscosity equal to 56.2 mPa·s and having an expected extensional viscosity of 168.6 mPa·s was used. The length of the thin wall stainless steel capillary was 5 cm and the inside diameter was 0.2159 cm. The drainage volume (V) was 200 cc. The measured extensional viscosity with respect to stretch rates is shown in Table 2.

TABLE 2

Measured extensional viscosity for Newtonian oil.

The two sets of data are for two experiments at different filament lengths. It is seen that the measured extensional viscosity is exactly what was expected at the capillary exit. However, the calculated value is somewhat higher than expected for most of the filament length. The deviation from the Trouton value at larger axial distances is due to end effects and also due to errors introduced by the very large contribution of the force of surface tension.

Procedure

Using the viscometer 100 shown in FIG. 1, extensional viscosity measurements were made for aqueous solutions of low molecular weight polymers. Water-soluble polyethylene oxide (PEO) of molecular weight (MW) 400,000 was obtained from Union Carbide. Two solutions of concentration 10 gm/liter and 5 gm/liter were prepared. A Carri-Med CSL100 controlled stress rheometer was used to determine the shear flow behavior of the two solutions. The shear stress could be measured between the shear rates of 10 and 3000 $s^{-1}$ and is shown in Table 3. A power law model was fitted to the date and power law coefficients.

TABLE 3

Shear flow behavior of PEO solutions.

For extensional viscosity measurements, the amount of solution required is about 225 mL including the drainage volume of 200 mL. It should be noted that the amount of solution required to make the measurement can be changed by selecting the proper length and diameter of the capillary through which the liquid drains. It is found that less amount of the solution is required if it has high elasticity or if high stretch rates can be obtained by using a finer capillary provided that the liquid does not drip. For both the concentrated and the dilute solution, a 5 cm long capillary was employed. The inside diameter in the two cases was 0.16 cm and 0.127 cm respectively. For both solutions, values for free flow drainage time ($t_1$) and stretched drainage time ($t_2$) are shown in Table 4.

TABLE 4

Drainage time for polymer solutions.

| solution | $t_1$ (sec) | $t_2$ (sec) |
| --- | --- | --- |
| 5 gm/lt | 354.80 | 351.99 |
|  | 345.25 | 344.07 |
| 10 gm/lt | 400.91 | 392.13 |
|  | 394.14 | 389.67 |

Experiments were performed for two sets of stretch rates for each solution. Extensional viscosity measurements, as a function of the stretch rate, are shown for the two solutions in Tables 5 and 6 respectively. As can be seen, stretch rates of 4000 $s^{-1}$ are obtainable. It is also observed that the extensional viscosity increases with an increase in the rate of stretching, a behavior that is expected from the theory of polymer solutions.

TABLE 5

Apparent extensional viscosity vs. stretch rate for 10 gm/liter PEO solution.

TABLE 6

Apparent extensional viscosity vs. stretch rate for 5 gm/liter PEO solution.

Calculations (a) Sample Calculation for Newtonian Oil.

density $\rho=0.85$ gm/cc; shear viscosity $\eta=0.56$ poise
drainage time without stretching $t_1=514.82$ seconds
drainage time with stretching $t_2=509.6$ seconds
upper capillary inside diameter (ID)=0.2159 cm; inside radius=0.1079 cm
filament profile $r=0.1141-0.8503x+1.7439x^2+1.079x^3$
$(dr/dx)_{x=0}=-0.8503$; $r|_{x=0}=0.1141$ cm
volumetric flow rate $Q=200/509.6=0.392$ cc/s
$\sigma_{ext}=(8*0.56*200*5)/(\pi(0.1141)^4)*\{1/509.6-1/514.82\}=208.947$ dynes/cm$^2$
stretch rate=$(2Q/\pi r_0^3)(-dr/dx)_{x=0}=(2*0.392/p*0.1141^3)(0.8503)=143.02$ s$^{-1}$
extensional viscosity at the exit=$208.947/143.02=1.46$ poise Now, force balance at point 1
$F_1=F_0+F_1(ST)-F_1(g)+F_1(I)$
Force at the upper capillary $F_0=\pi r_0^2 * \sigma_{ext}=3.1415*(0.1141)^2*208.947=8.546$ dynes
Surface tension at $x_1 F_1(ST)=2\pi\sigma_{ST}(r_0 \cos\theta_0 - r_1 \cos\theta_1)$
where $\theta_0=-\tan^{-1}[dr/dx|_{x=0}]=-\tan^{-1}(-0.8503+1.7439*2*x_0+3*1079*x_0^2)=0.7406$ radians
$\theta_1=-\tan^{-1}[dr/dx|_{x=1}]=-\tan^{-1}(-0.8503+1.7439*2*x_1+3*1.079*x_1^2)=0.676$ radians
$F_1(ST)=2\pi*28.5[0.1141 \cos(0.7406)-0.1028 \cos(0.676)]=1.204$ dynes
$F_1(g)=\rho g \pi[(r_0+r_1)/2]^2(x_1-x_0)=0.85*981*x*\pi*[(0.1141+0.1028)/2]^2(0.0367-0)=0.426$ dynes
$F_1(I)=\rho Q(v_1-v_0)$
$v_1=Q/\pi r_1^2=0.392/\pi(0.1028)^2=11.806$ cm/s
$v_0=Q/\pi r_0^2=0.392/\pi(0.1141)^2=9.584$ cm/s
$F_1(I)=0.7403$ dynes
$F_1=8.546+1.204-0.426+0.7403=10.064$ dynes
$T_1(11)=F_1/(\pi r_1^2)=10.064/(\pi*0.10282^2)=303.1197$ dynes/cm$^2$
$P(11)-P(22)=T_1(11)+\sigma_{ST}/r_1=303.1197+28.5/0.1028=580.34$ dynes/cm$^2$
stretch rate at $x_1 \epsilon|_{x=x1}=2*Q/\pi r_1^3)(-dr/dx|_{x=x1})=2*0.392*(0.802)/\pi(0.1028)^3=184.212$ s$^{-1}$
extensional viscosity $\theta_e=580.34/184.212=3.15$ poise=315 mPa·s For point 2
$F_2=F_1+F_2(ST)-F_2(g)+F_2(I)$
$R_2=0.092$ cm, $x_2=0.027$ cm
$\theta_2=0.645$ radians, $v_2=14.685$ cm/s
$F_2(ST)=1.172$ dynes, $F_2(g)=0.344$ dynes, $F_2(I)=0.959$ dynes
$F_2=11.851$ dynes
$T_2(11)=11.851/(\pi*r_2^2)=443.982$ dynes/cm$^2$
$P(11)-P(22)=753.165$ dynes/cm$^2$
stretch rate at $x_2 \epsilon_2=2*0.392*(0.7525)/\pi*0.092^3=239.78$ s$^{-1}$
extensional viscosity at $x_2=753.165/239.78=3.141$ poise=314.1 mPa·s (b) Sample Calculation for 10 gm/liter PEO Solution
$Q_0=200/401.08=0.4986$ cc/s
$Q_1=200/392.13=0.51$ cc/s
Power law coefficients $K=0.2612$, $n=0.8783$
From equations 2 and 3 we get $\sigma_{ext}=354.217$ dynes/cm$^2$
filament profile $r=0.0659-0.5104x-1.26x^2+28.99x^3$
$dr/dx|_{x=0}=-0.5104$, $x=0=0.0659$ cm
stretch rate=579.07 s$^{-1}$
extensional viscosity at the exit=354.217/579.07=0.612 poise=61.2 mPa·s
Now force balance at point 1
$F_1=F_0+F_1(ST)-F_1(g)+F_1(I)$
Force at the exit of upper capillary $F_0=\pi r_0^2*\sigma_{ext}=3.1415*(0.0659)^2*354.217=4.832$ dynes
Surface tension at $x_1 F_1(ST)=2\pi\sigma_{ST}(r_0 \cos\theta_0-r_1 \cos\theta_1)$
where $\theta_0=-\tan^{-1}[dr/dx|_{x=0}]=-\tan^{-1}(-0.5104-1.26*2*x_0+3*28.99*x_0^2)=0.472$ radians
$\theta_1=-\tan^{-1}[dr/dx|_{x=1}]=-\tan^{-1}(-0.5104-1.26*2*x_1+3*28.99*x_1^2)=0.483$ radians
$F_1(ST)=2\pi*70*[0.0659 \cos(0.472)-0.0615 \cos(0.483)]=1.854$ dynes
$F_1(g)=\rho g \pi[(r_0+r_1)/2]^2(x_1-x_0)=1*981*\pi*[(0.0659+0.0615)/2]^2(0.0084-0)=0.105$ dynes
$F_1(I)=\rho Q(v_1-v_0)$
$v_1=Q/\pi r_1^2=0.51/\pi(0.0615)^2=42.86$ cm/s
$v_0=Q/\pi r_0^2=0.51/\pi(0.0659)^2=37.38$ cm/s
$F_1(I)=2.794$ dynes $F_1=4.832+1.854-0.105+2.794=9.375$ dynes
$T_1(11)=F_1/(\pi r_1^2)=9.375/(\pi*0.0615^2)=787.906$ dynes/cm$^2$
$P(11)-P(22)=T_1(11)+\sigma_{ST}/r^1=787.906+70/0.0615=1925.299$ dynes/cm$^2$
stretch rate at $x_1\epsilon|_{x=x1}=2*Q/\pi r_1^3(-dr/dx|_{x=x1})=2*0.51*(0.52)/\pi(0.0615)^3=731.84$ s$^{-1}$
extensional viscosity $\eta_e=1925.299/731.84=2.63$ poise=263 mPa·s For point 2
$F_2=F_1+F_2(ST)-F_2(g)+F_2(I)$
$r_2=0.057$ cm, $x_2=0.0168$ cm
$\theta_2=0.485$ radians, $v_2=49.768$ cm/s
$F_2(ST)=1.75$ dynes, $F_2(g)=0.0911$ dynes, $F_2(I)=3.523$ dynes
$F_2=14.577$ dynes
$T_2(11)=14.577/(\pi*r_2^2)=1420.56$ dynes/cm$^2$
$P(11)-P(22)=2646.182$ dynes/cm$^2$
stretch rate at $x_2\epsilon_2=2*0.51*(0.528)/\pi*0.0615^3=920.51$ s$^{-1}$
extensional viscosity at $x_2=2646.182/920.51=2.874$ poise=287.4 mPa·s

CONCLUSION

While various embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A method for determining tensile stress within a liquid, comprising the steps of:
    (a) measuring the liquid's gravity-driven drainage time;
    (b) measuring the liquid's stretched drainage time; and
    (c) calculating the tensile stress of the liquid as a function of the difference between the liquid's gravity-driven drainage time and the liquid's stretched drainage time.

2. The method according to claim 1, wherein said step (a) comprises the steps of:
    (a1) filling a reservoir with a known amount of the liquid; and
    (a2) draining said reservoir by allowing the liquid to pass through a capillary attached to said reservoir; and
    (a3) measuring how long it takes to drain said reservoir.

3. The method according to claim 1, wherein said step (b) comprises the steps of:
    (b1) filling a reservoir with a known amount of the liquid;
    (b2) draining said reservoir by allowing the liquid to pass through a first capillary attached to said reservoir;
    (b3) drawing the liquid as it emerges from said first capillary into a second capillary, wherein said second capillary is positioned below said first capillary such that a gap exists between said first capillary and said second capillary; and
    (b4) measuring how long it takes to drain said reservoir.

4. The method according to claim 3, wherein each of said first and second capillaries has a diameter such that the diameter of said second capillary is equal to or less than the diameter of said first capillary.

5. The method according to claim 1, wherein the difference between the liquid's stretched drainage time and the liquid's gravity-driven drainage time is at least one second.

6. A method for determining extensional viscosity of a solution, comprising the steps of:
    (a) calculating tensile stress within the solution;
    (b) calculating the solution's stretch rate; and
    (c) calculating extensional viscosity of the solution as a ratio of tensile stress to stretch rate.

7. The method according to claim 6, wherein said step (a) comprises the steps of:
    (a) measuring the liquid's gravity-driven drainage time;
    (b) measuring the liquid's stretched drainage time; and
    (c) calculating the tensile stress of the liquid as a function of the difference between the liquid's gravity-driven drainage time and the liquid's stretched drainage time.

8. The method according to claim 7, wherein said step (a) comprises the steps of:
    (a1) filling a reservoir with a known amount of the solution; and
    (a2) draining said reservoir by allowing the solution to pass through a capillary attached to said reservoir; and
    (a3) measuring how long it takes to drain said reservoir.

9. The method according to claim 7, wherein said step (b) comprises the steps of:
    (b1) filling a reservoir with a known amount of the solution;
    (b2) draining said reservoir by allowing the solution to pass through a first capillary attached to said reservoir;
    (b3) suctioning the solution as it emerges from said first capillary into a second capillary positioned below said first capillary such that a gap exists between said first capillary and said bottom capillary; and
    (b4) measuring how long it takes to drain the reservoir.

10. The method according to claim 8, wherein each of said first and second capillaries has a diameter and the diameter of said second capillary is equal to or less than the diameter of said first capillary.

11. The method according to claim 7, wherein the difference between the solution's stretched drainage time and the solution's gravity-driven drainage time is at least one second.

12. An extensional viscometer for measuring tensile stress within a liquid, comprising:
    a liquid reservoir without a pressure measuring device;
    a first capillary through which liquid drains, connected to said liquid reservoir; and
    a second capillary positioned beneath said first capillary thereby creating a gap between said first and second capillaries, such that the liquid is stretched as it passes from said first capillary to said second capillary.

13. The extensional viscometer according to claim 12, further comprising a water bath in which said liquid reservoir is immersed.

14. The extensional viscometer according to claim 13, further comprising a circulator for maintaining said water bath at a constant temperature.

15. The extensional viscometer according to claim 12, wherein each of said first and second capillaries has a diameter and the diameter of said second capillary is equal to or less than the diameter of said first capillary.

16. The extensional viscometer according to claim 12, wherein said liquid reservoir has a first mark and a second mark.

17. The extensional viscometer according to claim 16, wherein a collection area is positioned between said first mark and said second mark.

18. A method for determining extensional viscosity of a liquid, comprising the step of:
(a) inferring fluid stress by measuring change in flow rate of the liquid during passage through a vertical capillary, wherein the change in flow rate is calculated by: determining the liquid's gravity-driven flow rate; determining the liquid's stretched flow rate; and subtracting the stretched flow rate from the gravity-driven flow rate.

19. The method according to claim 18, wherein the stretched flow rate of the liquid is determined by positioning a second capillary beneath a first capillary, such that said second capillary creates a force that pulls the liquid from said first capillary into said second capillary.

20. The method according to claim 19, wherein each of said first and second capillaries has a diameter and the diameter of said second capillary is equal to or less than the diameter of said first capillary.

* * * * *